(12) United States Patent
Kim et al.

(10) Patent No.: US 9,746,430 B2
(45) Date of Patent: Aug. 29, 2017

(54) OPTICAL INSPECTING APPARATUS

(71) Applicant: SAMSUNG ELECTRONICS CO., LTD., Suwon-si, Gyeonggi-Do (KR)

(72) Inventors: Tae-Joong Kim, Hwaseong-si (KR); Young-Kyu Park, Incheon (KR); Ki-Jung Son, Suwon-si (KR); Byeong-Hwan Jeon, Yongin-si (KR); Chang-Hoon Choi, Suwon-si (KR)

(73) Assignee: SAMSUNG ELECTRONICS CO., LTD., Suwon-si, Gyeonggi-Do (KR)

( * ) Notice: Subject to any disclaimer, the term of this patent is extended or adjusted under 35 U.S.C. 154(b) by 9 days.

(21) Appl. No.: 14/823,343

(22) Filed: Aug. 11, 2015

(65) Prior Publication Data
US 2016/0153918 A1    Jun. 2, 2016

(30) Foreign Application Priority Data
Dec. 1, 2014  (KR) .................. 10-2014-0169975

(51) Int. Cl.
*G01N 21/00* (2006.01)
*G01N 21/956* (2006.01)
*G01N 21/958* (2006.01)

(52) U.S. Cl.
CPC ......... *G01N 21/956* (2013.01); *G01N 21/958* (2013.01); *G01N 2021/95676* (2013.01)

(58) Field of Classification Search
CPC ............... G01N 21/956; G01N 21/958; G01N 2021/95676; G01N 21/95607; G01N 21/8806; G02B 21/0024; G02B 21/008; G02B 21/006; G06T 2207/30148

USPC ........................................... 356/237.2–237.6
See application file for complete search history.

(56) References Cited

U.S. PATENT DOCUMENTS

| | | | |
|---|---|---|---|
| 3,715,165 | A * | 2/1973 | Smith ............... G01B 11/30 356/365 |
| 4,532,650 | A | 7/1985 | Wihl et al. |
| 5,572,598 | A | 11/1996 | Wihl et al. |
| 5,742,386 | A | 4/1998 | Nose et al. |

(Continued)

FOREIGN PATENT DOCUMENTS

| JP | 2003-140050 | 5/2003 |
|---|---|---|
| JP | 2007-256577 | 10/2007 |

(Continued)

*Primary Examiner* — Tarifur Chowdhury
*Assistant Examiner* — Isiaka Akanbi
(74) *Attorney, Agent, or Firm* — F. Chau & Associates, LLC

(57) ABSTRACT

An optical inspecting apparatus includes a first light source, a beam splitter, a first lens, a first light detector, and pinhole plates. The first light source emits a first light beam. The beam splitter transmits or reflects the first light beam. The first lens provides the first light beam to transmit through a transparent substrate of a photomask and forms a first focusing spot on a first surface of the transparent substrate or a top surface of a photomask pattern formed on the transparent substrate. The first light detector detects a first reflection light beam generated by reflecting the first light beam from the first surface of the transparent substrate or the top surface of the photomask pattern. The pinhole plates are disposed in front of the first light detector to filter noise in the reflection light beam.

7 Claims, 9 Drawing Sheets

(56) References Cited

U.S. PATENT DOCUMENTS

| | | | |
|---|---|---|---|
| 5,764,363 A * | 6/1998 | Ooki | G01B 11/0608 |
| | | | 356/364 |
| 6,052,478 A | 4/2000 | Wihl et al. | |
| 6,445,453 B1 * | 9/2002 | Hill | G01Q 60/22 |
| | | | 356/450 |
| 6,654,110 B2 | 11/2003 | Yonezawa et al. | |
| 6,665,065 B1 | 12/2003 | Phan et al. | |
| 7,205,549 B2 * | 4/2007 | Yoshida | G01N 21/956 |
| | | | 250/307 |
| 7,252,910 B2 | 8/2007 | Hasegawa et al. | |
| 7,630,538 B2 | 12/2009 | Nishiyama et al. | |
| 7,724,361 B2 | 5/2010 | Tanaka | |
| 8,064,059 B2 | 11/2011 | Vaziri | |
| 8,228,497 B2 | 7/2012 | Mangan et al. | |
| 8,711,346 B2 | 4/2014 | Stokowski | |

FOREIGN PATENT DOCUMENTS

| | | |
|---|---|---|
| JP | 2008-134214 | 6/2008 |
| JP | 2010-026344 | 2/2010 |
| JP | 2010-044310 | 2/2010 |
| JP | 2010-045283 | 2/2010 |
| JP | 2011-197288 | 10/2011 |
| KR | 1020090072808 | 7/2009 |
| KR | 1020100066820 | 6/2010 |

\* cited by examiner

OPTICAL INSPECTING APPARATUS

CROSS-REFERENCE TO RELATED APPLICATION

This application claims priority under 35 U.S.C. §119 to Korean Patent Application No. 10-2014-0169975, filed on Dec. 1, 2014, in the Korean Intellectual Property Office, the disclosure of which is incorporated by reference herein in its entirety.

TECHNICAL FIELD

The present inventive concept relates to an optical inspecting apparatus, and more particularly, to an optical inspecting apparatus including a confocal microscope.

DISCUSSION OF THE RELATED ART

A photomask is used in a photolithography process to form a pattern on a semiconductor wafer. In general, since a single photomask may be used in common to manufacture a plurality of semiconductor devices, even a microscopic defect on the photomask may deteriorate a semiconductor device.

An optical inspecting apparatus may be used to inspect whether a photomask is defective or not. This is accomplished by irradiating light beams onto the photomask under inspection and capturing an image corresponding to light reflected from a surface of the photomask.

SUMMARY

According to an exemplary embodiment of the present inventive concept, an optical inspecting apparatus is provided. The apparatus includes a first light source, a beam splitter, a first lens, a first light detector, and pinhole plates. The first light source emits a first light beam. The beam splitter transmits or reflects the first light beam. The first lens provides the first light beam to transmit through a transparent substrate of a photomask and forms a first focusing spot on a first surface of the transparent substrate or a top surface of a photomask pattern formed on the transparent substrate. The first light detector detects a first reflection light beam generated by reflecting the first light beam by the first surface of the transparent substrate or the top surface of the photomask pattern. The pinhole plates are disposed in front of the first light detector to filter noise in the reflection light beam.

The first light source may be a point light source, and the first light beam may be converted into parallel rays and incident on the beam splitter.

The photomask pattern may be formed on the first surface of the transparent substrate, and the first light beam may be incident on a second surface of the transparent substrate opposite to the first surface.

The photomask may be disposed on a horizontal stage, and edges of the transparent substrate may contact supports disposed on the horizontal stage so that the photomask pattern does not directly contact the horizontal stage.

The first light beam may have a wavelength in an infrared wavelength range.

The apparatus may further include a second light source and a second light detector. The second light source may emit a second light beam having a second polarization direction different from a first polarization direction of the first light beam or a second wavelength different from a first wavelength of the first light beam. The second light detector may detect a second reflection light beam generated by reflecting the second light beam by a portion of the photomask.

A plurality of light beams emitted from a plurality of light sources including the first light source and the second light source may transmit through the transparent substrate and may form a plurality of different focusing spots from each other on the first surface of the transparent substrate or the top surface of the photomask pattern formed on the transparent substrate.

The apparatus may further include a resonant mirror disposed between the beam splitter and the photomask. The resonant mirror may rotate such that the plurality of light beams scans the photomask. A scanning direction of the photomask may be substantially perpendicular to a direction in which the plurality of different focusing spots is formed.

The apparatus may further include a polarizing beam splitter that splits the first light beam and the second light beam.

The apparatus may further include a third light source and a fourth light source. The third light source may emit a third beam having the first polarization direction and a third wavelength different from the first wavelength. The fourth light source may emit a fourth light beam having the second polarization direction and a fourth wavelength different from the second wavelength.

The first to fourth light beams may transmit through the transparent substrate and respectively form first to fourth focusing spots on the first surface of the transparent substrate or the top surface of the photomask pattern formed on the transparent substrate.

The apparatus may further include a dichroic mirror that splits the first and second light beams.

The apparatus may further include a vertical stage disposed between the beam splitter and the first lens. The vertical stage may adjust a distance between the photomask and the first lens.

According to an exemplary embodiment of the present inventive concept, an optical inspecting apparatus is provided. The apparatus includes a plurality of light sources, a beam splitter, a first lens, and a plurality of light detectors. The plurality of light sources emits a plurality of light beams. The beam splitter transmits or reflects the plurality of light beams. The first lens focuses the plurality of light beams and forms the plurality of different focusing spots on the portion of the inspection target. The plurality of light detectors detects a plurality of reflection light beams generated by reflecting the plurality of light beams by the inspection target. At least two of the plurality of light beams have different polarization directions from each other or different wavelengths from each other.

The inspection target may include a first surface and a second surface opposite to the first surface. The plurality of light beams may be incident on the second surface and may form the plurality of different focusing spots from each other on the first surface. The plurality of reflection light beams may correspond to an image of the first surface.

According to an exemplary embodiment of the present inventive concept, an optical inspecting apparatus is provided. The apparatus includes a first light source, a second light source, a first lens, a first beam splitter, a first light detector, and a second light detector. The first light source emits a first light beam having a first polarization direction. The second light source emits a second light beam having a second polarization direction different from the first polarization direction. The first lens faces a first surface of a photomask, and forms a first focusing spot of the first light beam and a second focusing spot of the second light beam on a second surface of the photomask opposite to the first surface. The first beam splitter divides a first reflection light beam and a second reflection light beam reflected from the second surface of the photomask. The first light detector detects the first reflection light beam reflected from the second surface of the photomask. The second light detector detects the second reflection light beam reflected from the second surface of the photomask. A photomask pattern is formed on the second surface of the photomask. Each of the first and second light beams has a wavelength in an infrared range.

The apparatus may further include pinhole plates disposed in front of the first light detector to filter noise in the first reflection light beam reflected from the second surface of the photomask.

The apparatus may further include a second beam splitter that transmits or reflects the first and second light beams.

The first light source may be a point light source, and the first light beam may be converted into parallel rays and incident on the second beam splitter.

The first and second focusing spots may move in a first direction toward an edge on the second surface, and may move in a second direction in which the first and second focusing spots are arranged. The first direction may be substantially perpendicular to the second direction.

BRIEF DESCRIPTION OF THE DRAWINGS

Exemplary embodiments of the present inventive concept will be more clearly understood from the following detailed description taken in conjunction with the accompanying drawings in which.

DETAILED DESCRIPTION OF THE EMBODIMENTS

Figure 1:
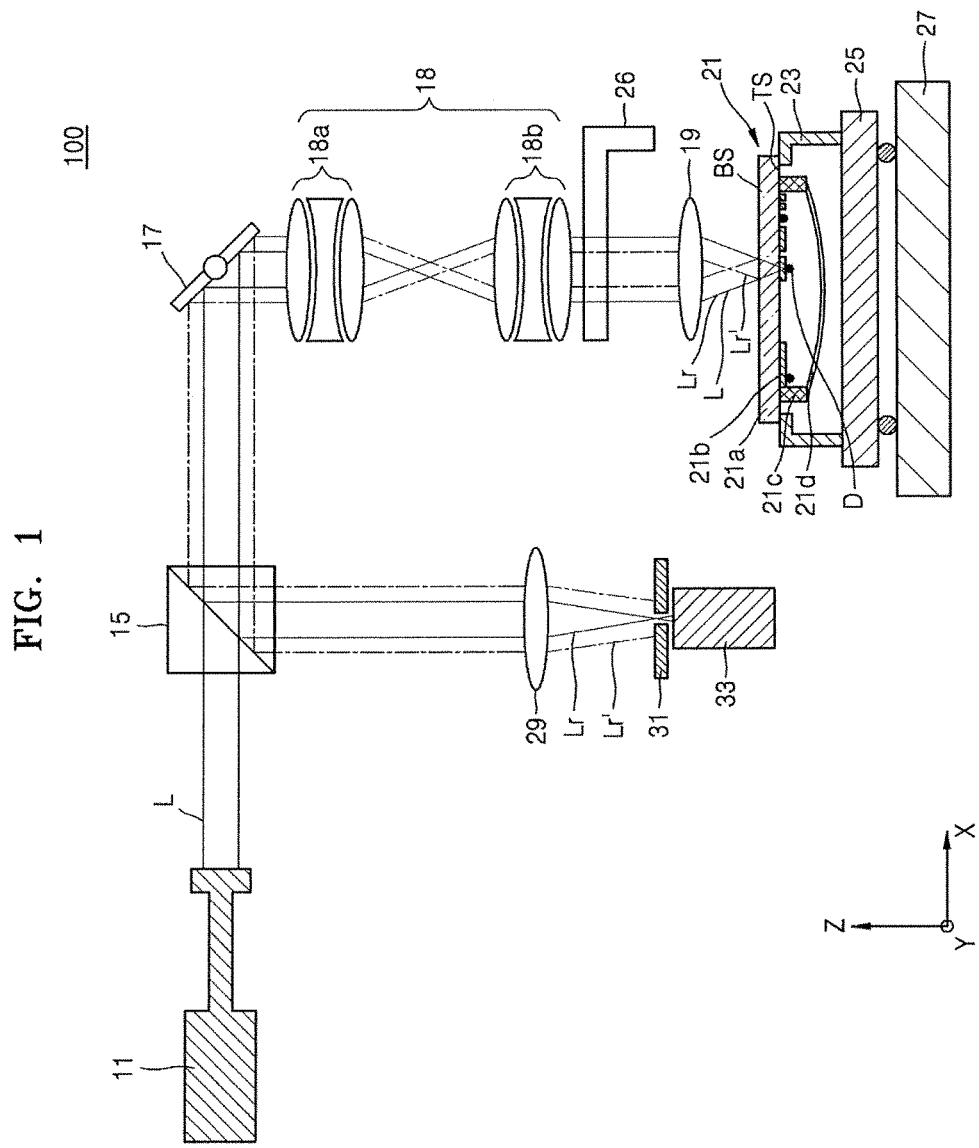
FIG. 1 is a diagram illustrating an optical inspecting apparatus according to an exemplary embodiment of the present inventive concept.

Exemplary embodiments of the present inventive concept will now be described more in detail with reference to the accompanying drawings.

The present inventive concept may be embodied in various forms and should not be construed as being limited to the embodiments set forth herein. In the drawings, the size and relative sizes of layers, regions, or components may be exaggerated for clarity. Like numbers may refer to like elements throughout the specification and drawings.

FIG. 1 is a diagram illustrating an optical inspecting apparatus 100 according to an exemplary embodiment of the present inventive concept.

Referring to FIG. 1, the optical inspecting apparatus 100 inspects whether a photomask 21, which is an inspection target, is defective. The optical inspecting apparatus 100 may include a light source 11 that emits a light beam L, a beam splitter 15 that reflects the light beam L or splits parallel rays from the light beam L, a resonant mirror 17 that changes a path of the light beam L, a relay optical system 18 that adjusts a size of the light beam L, an objective lens 19 that incidents the light beam L on a bottom surface BS of the photomask 21 and forms a focus on a top surface TS of the photomask 21, supports 23 that contact edges of the top surface TS of the photomask 21, a horizontal stage 25 on which the supports 23 are disposed, a vertical stage 26 that vertically moves the objective lens 19, a condensing lens 29 that focuses a reflection light beam Lr reflected from the photomask 21, a light detector 33 that detects the reflection light beam Lr, and pinhole plates 31 that are disposed in front of the light detector 33 and that remove noise.

For example, the optical inspecting apparatus 100 performs a defect inspection by moving the optical system including the light source 11, the beam splitter 15, the resonant mirror 17, the relay optical system 18, and the objective lens 19 toward the bottom surface BS of the photomask 21 that is opposite to the top surface TS of the photomask 21, which is a surface to be captured. When the optical system is moved near the bottom surface BS of the photomask 21, a shadow area may not be created on the top surface TS of the photomask 21 to be captured, and thus, a defect inspection may be performed on the whole area of the photomask 21.

The light source 11 may emit the light beam L toward the beam splitter 15. The light source 11 may include a point light source. The light beam L emitted from the point light source may be converted into parallel rays through a collimating lens and may be incident to the beam splitter 15. Therefore, the optical inspecting apparatus 100 may be a confocal optical system in which a focus of the light source 11, a focus formed on the top surface TS of the photomask 21, and a focus formed on the light detector 33 coincide with one another. The confocal optical system may reduce an effect caused by noise which may be generated from the light beam L as the optical system approaches the bottom surface BS of the photomask 21. A pinhole plate may be further included in front of the light source 11 that emits the light beam L, and thus, noise may be blocked. In an exemplary embodiment of the present inventive concept, the light beam L may be parallel rays generated by a laser source.

The light beam L emitted from the light source 11 may have a single wavelength, but the present inventive concept is not limited thereto. In an exemplary embodiment of the present inventive concept, the light beam L may include a plurality of wavelengths within an infrared range. For example, the optical inspecting apparatus 100 may include a light source that emits infrared light having a plurality of wavelengths in a range from about 780 nm to about 1 mm. Since the light beam L including the wavelengths in the infrared range may have a relatively high transmittance through a photomask pattern 21b, a relatively clear image may be obtained. This will be described in detail with reference to FIG. 3.

The beam splitter 15 may transmit parallel rays from among the light beam L emitted from the light source 11. The light beam L that is transmitted through the beam splitter 15 may be incident on the resonant mirror 17 that adjusts an angle of the light beam L.

The resonant mirror 17 may change a path of the light beam L by rotating, and thus, a focusing location of the light beam L that is formed on the top surface TS of the photomask 21 may be moved. An image of the whole area of the photomask 21 may be obtained through the resonant mirror 17 that continuously rotates. Whether the photomask 21 is defective may be identified based on the obtained image. The resonant mirror 17 is an example of a 2-dimensional (2D) scanner for obtaining the image of the whole area of the photomask 21. However, the resonant mirror 17 is not limited thereto. In an exemplary embodiment of the present inventive concept, the 2D scanner may be the horizontal stage 25 that may change the location of the focus of the light beam L by changing a position of the photomask 21. Although FIG. 1 illustrates the resonant mirror 17 and the horizontal stage 25 as the 2D scanner, any one of the resonant mirror 17 and the horizontal stage 25 may be omitted. For example, when the horizontal stage 25 is omitted, a stage may be provided to support an inspection target.

The relay optical system 18 may include a first relay lens 18a and a second relay lens 18b, and adjust the size of the light beam L according to the size of the photomask 21 that is the inspection target.

Although FIG. 1 illustrates that two relay lenses (e.g., the first and second relay lenses 18a and 18b) are included in the relay optical system 18, exemplary embodiments of the present inventive concept are not limited thereto. For example, one or more than two relay lenses may be included in the relay optical system 18.

The objective lens 19 may be disposed between the relay optical system 18 and the photomask 21. The objective lens 19 may allow the light beam L to be incident on the bottom surface BS of the photomask 21, to be transmitted through the photomask 21, and to form a focus on the top surface TS of the photomask 21. The focus (e.g., the focusing location of the light beam L) may be determined based on properties of the objective lens 19 and wavelengths of the light source 11. In FIG. 1, the focus is formed at a defect D attached on the photomask pattern 21b. When a focus is formed on the top surface TS of the photomask 21, a moving path of the reflection light beam Lr reflected from the focus is determined. In this case, the light source 11, the focus of the top surface TS of the photomask 21, and a focus formed on the light detector 33 are in a conjugate relationship. Such conjugation is a property of the above-described confocal optical system.

The photomask 21, which is the inspection target, is disposed on the horizontal stage 25. The supports 23 are disposed on the horizontal stage 25 and support the photomask 21. For example, the photomask 21, which is the inspection target to be inspected by the optical inspecting apparatus 100, may include a transparent substrate 21a, the photomask pattern 21b formed on the transparent substrate 21a, pellicle supports 21c disposed at edges of the transparent substrate 21a to prevent the photomask pattern 21b from being harmed by external substances, and a pellicle 21d formed on the pellicle supports 21c. The optical inspecting apparatus 100 may include the supports 23 on the horizontal stage 25 so that the top surface TS of the photomask 21 does not directly contact the horizontal stage 25. The supports 23 protect the photomask pattern 21b and the pellicle 21d when the top surface TS of the photomask 21 faces the horizontal stage 25. For example, the supports 23 only support the edges of the transparent substrate 21a such that the photomask pattern 21b and the pellicle 21d do not directly contact the horizontal stage 25.

Although FIG. 1 illustrates the photomask 21 as the inspection target to be inspected by the optical inspecting apparatus 100, exemplary embodiments of the present inventive concept are not limited thereto. The optical inspecting apparatus 100 may reduce an effect of a shadow area which may be generated by a structure on a surface to be captured, and may be used to inspect the photomask 21 and an object including a structure on a surface to be captured. In an exemplary embodiment of the present inventive concept, when an inspection target (e.g., the photomask 21) has a first surface on which a structure is formed and a second surface opposite to the first surface, the supports 23 may be disposed to contact edges of the first surface of the inspection target so that the first surface of the inspection target does not directly contact the horizontal stage 25.

In an exemplary embodiment of the present inventive concept, the horizontal stage 25 may be moved on a plane (e.g., a plane defined by an X-axis direction and a Y-axis direction of FIG. 1). Since the photomask 21 is disposed on the horizontal stage 25, the whole area of the photomask 21 may be scanned by moving the horizontal stage 25, and thus, a 2D image may be obtained. In an exemplary embodiment of the present inventive concept, when the resonant mirror 17 is used as a 2D scanner, the horizontal stage 25 may not be moved and may be fixed to a ground 27.

The vertical stage 26 may be connected to the objective lens 19 and may move the objective lens 19 in a vertical direction (e.g., a Z-axis direction of FIG. 1). Accordingly, a 3-dimensional (3D) image of the top surface TS of the photomask 21 may be obtained. The vertical stage 26 may adjust a height (e.g., a location in the Z-axis direction) of the objective lens 19 and find a location where a signal detected by the light detector 33 has a maximum value, and thus, an image of the defect D (e.g., impurities) on the top surface TS of the photomask 21 may be obtained. In an exemplary embodiment of the present inventive concept, the vertical stage 26 may be omitted, and the optical inspecting apparatus 100 may be vertically moved without using the vertical stage 26.

The reflection light beam Lr reflected by the top surface TS of the photomask 21 may travel over a path that is similar to that of when the light beam L is incident on the photomask 21. The reflection light beam Lr is converted into parallel rays while being transmitted through the objective lens 19.

The size of the reflection light beam Lr is adjusted while being transmitted through the relay optical system 18. The reflection light beam Lr may be reflected by the resonant mirror 17 and thus incident on the beam splitter 15. The beam splitter 15 may reflect the reflection light beam Lr to the condensing lens 29.

The condensing lens 29 may adjust the reflection light beam Lr such that the reflection light beam Lr forms a focus on the light detector 33. The pinhole plates 31 may be disposed in front of the condensing lens 29.

The pinhole plates 31 may block noise Lr' in the reflection light beam Lr. If the optical inspecting apparatus 100 operates such that the light beam L is transmitted through the bottom surface BS of the photomask 21 to capture the top surface TS of the photomask 21, a large amount of noise Lr' scattered from the bottom surface BS may be generated, and thus, image quality may decrease. Since the pinhole plates 31 may effectively block the noise Lr', a relatively clear image of the top surface TS of the photomask 21 may be obtained even if the transparent substrate 21a is thick.

Since the light source 11 includes the point light source, an image corresponding to a point of the photomask 21 may be obtained. Therefore, the optical inspecting apparatus 100 may include a 2D scanner to obtain an image corresponding to the whole area of the photomask 21. In this case, the horizontal stage 25, on which the photomask 21 is disposed, may scan by moving on the plane (e.g., a horizontal plane defined by the X-axis direction and the Y-axis direction of FIG. 1) as described above.

In an exemplary embodiment of the present inventive concept, an angle of the light beam L may be changed by adjusting a rotation angle of the resonant mirror 17 on which the light beam L is incident, and thus, the whole area of the photomask 21 may be scanned and a 2D image of the photomask 21 may be obtained. This will be described in detail with reference to FIG. 5.

Figure 2A:
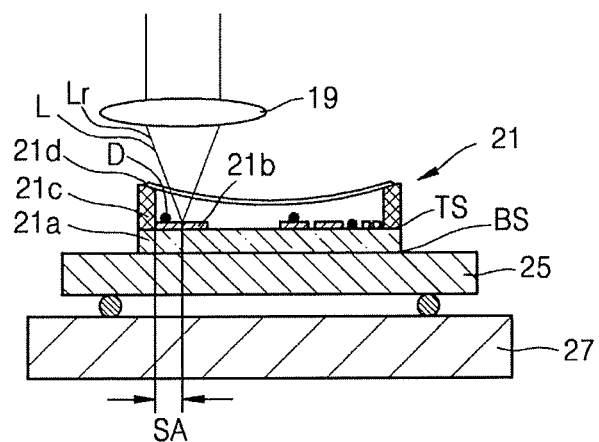
FIGS. 2A and 2B are diagrams for comparing photomask inspection processes performed by using a general optical inspecting apparatus and an optical inspecting apparatus according to an exemplary embodiment of the present inventive concept.
Figure 2B:
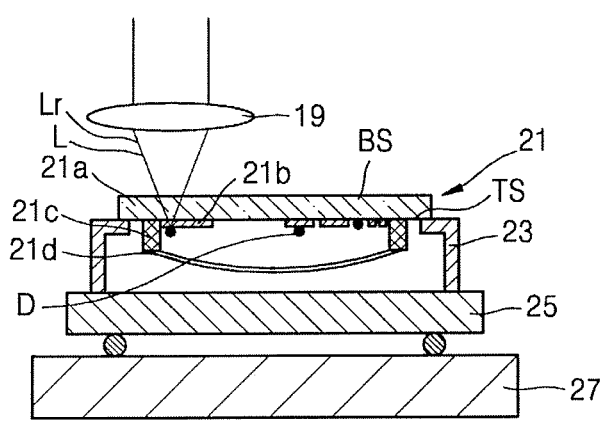

FIGS. 2A and 2B are diagrams for comparing photomask inspection processes performed by using a general optical inspecting apparatus and an optical inspecting apparatus according to an exemplary embodiment of the present inventive concept. FIGS. 2A and 2B illustrate a portion of the optical inspecting apparatus 100 which includes the horizontal stage 25 on which the photomask 21 is disposed, the photomask 21, and the objective lens 19 that focuses the light beam L on the photomask 21.

FIG. 2A illustrates an example of inspecting the photomask 21 by using the general optical inspecting apparatus. The photomask 21 is used in photolithography processes to form a pattern on a semiconductor wafer. Since a small defect on the photomask 21 may deteriorate a semiconductor device and a single photomask 21 is used in common to manufacture a plurality of semiconductor devices, the defect D including impurities on the photomask 21 may be eliminated to prevent the semiconductor devices from deteriorating and to reduce manufacturing cost.

The photomask 21 includes the transparent substrate 21a and the photomask pattern 21b formed on the transparent substrate 21a. To prevent a surface of the photomask pattern 21b from being harmed when the photomask 21 is moved, the pellicle supports 21c are disposed on edges of the transparent substrate 21a where the photomask pattern 21b is formed. In addition, the pellicle 21d may be formed on the pellicle supports 21c so that external substances do not affect the photomask pattern 21b.

Since only the horizontal stage 25, which is flat, is provided in the general optical inspecting apparatus, the bottom surface BS of the transparent substrate 21a, where the photomask pattern 21b is not formed, is disposed to contact the horizontal stage 25, and the light beam L is incident on the top surface TS of the transparent substrate 21a where the photomask pattern 21b is formed. In this case, since the pellicle supports 21c are disposed on the edges of the top surface TS of the transparent substrate 21a, the pellicle supports 21c may block the light beam L and create a shadow area SA at an area near one of the pellicle supports 21c. Therefore, the defect D such as impurities, or the like, in the shadow area SA may not be easily detected by using the general optical inspecting apparatus, and the defect D in the shadow area SA may have to be detected by the naked eye. Thus, in this case, detection performance of a defect and inspection speed of a photomask 21 of the general optical inspecting apparatus may be relatively low.

Referring to FIGS. 1 and 2B, the optical inspecting apparatus 100 according to an exemplary embodiment of the present inventive concept may emit the light beam L onto the bottom surface BS of the transparent substrate 21 where the photomask pattern 21b is not formed, the light beam L may be transmitted through the transparent substrate 21a, and thus, the top surface TS of the transparent substrate 21a (e.g., a surface where the photomask pattern 21b is formed) may be captured. On the horizontal stage 25 included in the optical inspecting apparatus 100, the supports 23 that contact the edges of the transparent substrate 21a and support the photomask 21 may be disposed so that the horizontal stage 25 does not directly contact the pellicle 21d. Since, in the optical inspecting apparatus 100, an optical system including the light source 11, the beam splitter 15, the resonant mirror 17, the relay optical system 18, and the objective lens 19 is moved to approach the bottom surface BS of the photomask 21, the shadow area SA of FIG. 2A is not created by the pellicle support 21c, and thus, the whole area of the photomask 21 may be inspected. Therefore, when inspecting the photomask 21 by using the optical inspecting apparatus 100 according to an exemplary embodiment of the present inventive concept, the shadow area SA of FIG. 2A does not have to be additionally inspected by using the naked eye, and thus, detection performance of a defect D and inspection speed of a photomask 21 may be increased.

In some cases, the photomask pattern 21b may not be formed at the edges of the transparent substrate 21a where the shadow area SA is created. However, when the photomask 21 is moved, the defect D such as floating impurities, or the like, in the shadow area SA may move to a central portion of the photomask 21 where the photomask pattern 21b is formed, and thus, the photomask pattern 21b may be harmed. Therefore, an accurate inspection of the shadow area SA may need to be performed regardless of whether the shadow area SA is formed in the photomask pattern 21b.

Figure 3:
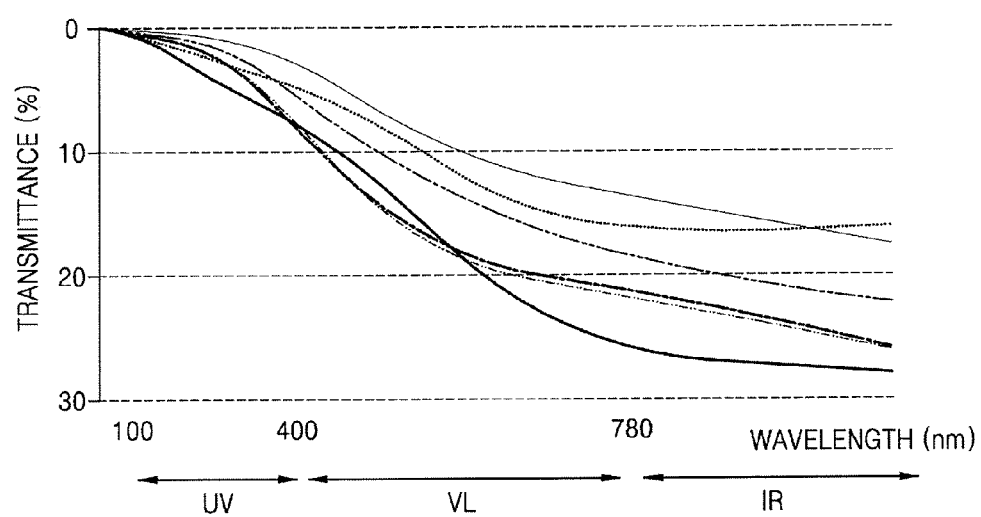
FIG. 3 is a graph illustrating a transmittance of a photomask substrate according to a wavelength of an incident light beam.

FIG. 3 is a graph illustrating a transmittance of a photomask pattern according to a wavelength of incident light beam L.

Referring to FIG. 3, the graph shows a transmittance of the photomask pattern 21b of FIG. 2 in an ultraviolet wavelength range UV of about 100 nm to about 400 nm, a visible light wavelength range VL of about 400 nm to about 780 nm, and an infrared wavelength range IR of about 780 nm to about 1 mm. When a light beam in the infrared wavelength range IR is emitted, the transmittance is about 15% to about 30%. Thus, an image captured by emitting a light beam in the infrared wavelength range IR may be clearer than those captured by emitting a light beam in the ultraviolet wavelength range UV and a light beam in the visible light wavelength range VL, in which the transmittance is about 10%.

In an exemplary embodiment of the present inventive concept, the optical inspecting apparatus 100 of FIG. 1 may include the light source 11 that emits the light beam L in the infrared wavelength range IR, and may inspect the photomask pattern 21b that includes a molybdenum silicide (MoSi) material.

Figure 4A:
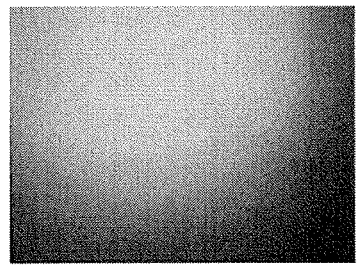
FIG. 4A is an image of a photomask captured by using a general optical inspecting apparatus.
Figure 4B:
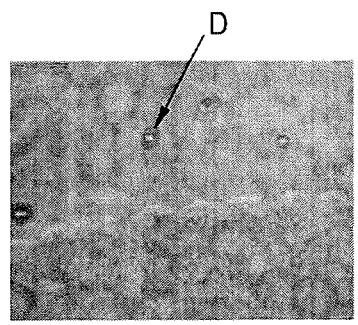
FIG. 4B is an image of a photomask captured by using an optical inspecting apparatus according to an exemplary embodiment of the present inventive concept.
Figure 4C:
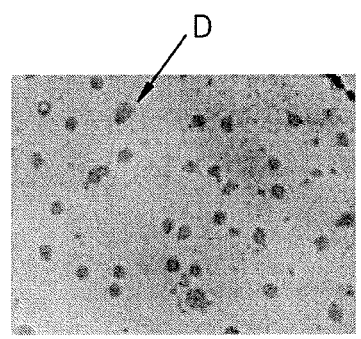
FIG. 4C is an image of a photomask captured by using an optical inspecting apparatus according to an exemplary embodiment of the present inventive concept.

FIG. 4A is an image of a photomask captured by using a general optical inspecting apparatus, FIG. 4B is an image of a photomask captured by using an optical inspecting apparatus 100 according to an exemplary embodiment of the present inventive concept, and FIG. 4C is an image of the photomask captured by using the optical inspecting apparatus 100 according to an exemplary embodiment of the present inventive concept. The images shown in FIGS. 4A to 4C are obtained by capturing an area near one of the pellicle supports 21c of FIGS. 2A and 2B where the shadow area SA may be formed.

Referring to FIGS. 4A and 2A, the photomask 21 is captured by using the general optical inspecting apparatus. The bottom surface BS of the photomask 21 is disposed to contact the horizontal stage 25 and the light beam L is incident on the top surface TS of the photomask 21. As described with reference to FIGS. 1 and 2A, the shadow area SA, where the light beam L is not incident, is formed by the pellicle supports 21c disposed on the top surface TS of the transparent substrate 21a, and an image of the shadow area SA may not be obtained. Therefore, whether the shadow area SA is defective may not be determined.

Referring to FIGS. 4B and 2B, the photomask 21 is captured by using the optical inspecting apparatus 100 according to an exemplary embodiment of the present inventive concept. The light beam L is not incident on the top surface TS of the photomask 21 where the photomask pattern 21b is formed and is incident on the bottom surface BS of the photomask 21. In this case, the shadow area SA by the pellicle supports 21c is not formed. Therefore, the whole area of the top surface TS of the photomask 21 may be inspected and the defect D near the pellicle supports 21c may be detected.

Referring to FIGS. 4C and 2B, the photomask 21 is captured by using the optical inspecting apparatus 100 according to an exemplary embodiment of the present inventive concept and the light source 11 emits light beams L in the infrared wavelength range IR. As described with reference to FIG. 3, since the transmittance of the light beam L in the infrared wavelength range IR through the photomask 21 is higher than that in other wavelength ranges, an image obtained when the light beam L is emitted in the infrared wavelength range IR may be clearer than that obtained when the light beam L is emitted in the ultraviolet wavelength range UV and/or the visible light wavelength range VL. Therefore, the defect D in the top surface TS of the photomask 21 may be detected. The image of FIG. 4B is captured by using the light source 11 that emits a light beam L having a wavelength of about 405 nm in the visible light wavelength range VL, and FIG. 4C is captured by using the light source 11 that emits a light beam L having a wavelength about 1300 nm in the infrared wavelength range IR. The image of FIG. 4C captured by using the light beam L in the infrared wavelength range IR may be clearer than the image of FIG. 4B captured by using the light beam L in the visible light wavelength range VL. For example, contrast between the defect D such as impurities, or the like, and a surface of the photomask 21 may be relatively high.

The defects D detected in the images of FIGS. 4B and 4C are gold nano-particles having a diameter of about 100 nm. Accordingly, it may be understood that the optical inspecting apparatus 100 may distinguish the defect D having a diameter of about 100 nm or less. Therefore, the inspection power of the optical inspecting apparatus 100 may be higher than that of the naked eye which is about 4 µm. In addition, since the optical inspecting apparatus 100 is an automatic apparatus, the inspection may be performed faster than the naked eye.

Figure 5:
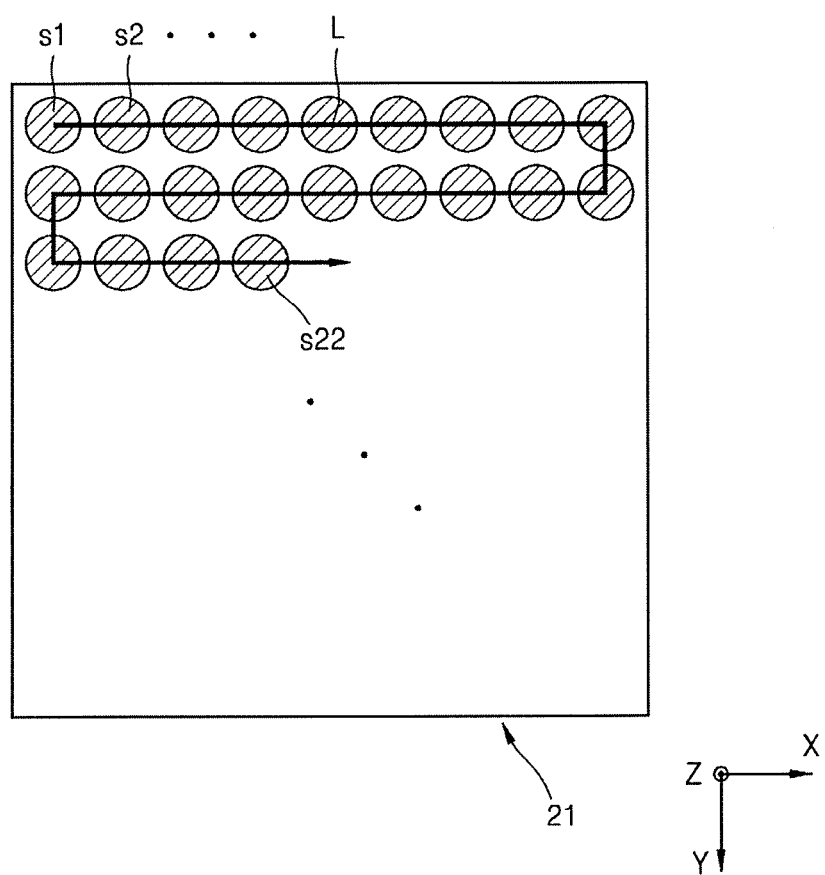
FIG. 5 is a diagram illustrating a scanning path on a photomask when the photomask is inspected by the optical inspecting apparatus of FIG. 1 according to an exemplary embodiment of the present inventive concept.

FIG. 5 is a diagram illustrating a scanning path on a photomask when the photomask is inspected by an optical inspecting apparatus 100 according to an exemplary embodiment of the present inventive concept.

Referring to FIGS. 1 and 5, the whole area of the photomask 21 may be scanned by adjusting a rotation angle of the resonant mirror 17 at which the light beam L is incident. In this case, a raster scanning scheme may be used. For example, when scanning of a first row including first and second spots s1 and s2 on the photomask 21 is finished, the next row (e.g., a second row) may be scanned in a horizontal direction (e.g., an X-axis direction). The resonant mirror 17 may be adjusted such that a focus of the light beam L moves in the horizontal direction and in a vertical direction (e.g., a Y-axis direction) to the next row when the scanning in the horizontal direction is finished. A first rotation speed when scanning in the horizontal direction may be faster than a second rotation speed when scanning in the vertical direction. A horizontal scanning speed and a vertical scanning speed may be determined respectively based on the first rotation speed and the second rotation speed. In an exemplary embodiment of the present inventive concept, the horizontal scanning speed may be 1,000 times faster than the vertical scanning speed. However, exemplary embodiments of the present inventive concept are not limited thereto.

According to an exemplary embodiment of the present inventive concept, other than the light source 11 and the light detector 33, the optical inspecting apparatus 100 may further include at least one light source and a first light detector. The at least one light source emits a light beam that is different in at least one of a polarization direction and a wavelength from those of the light emitted by the light source 11. The first light detector detects reflection light beam generated by the at least one light source. In this case, in the optical inspecting apparatus 100, a plurality of focuses may be formed by the plurality of light sources, and accordingly, the photomask 21 may be inspected at a relatively fast speed. This will be described in detail with reference to FIGS. 6 and 9.

Figure 6:
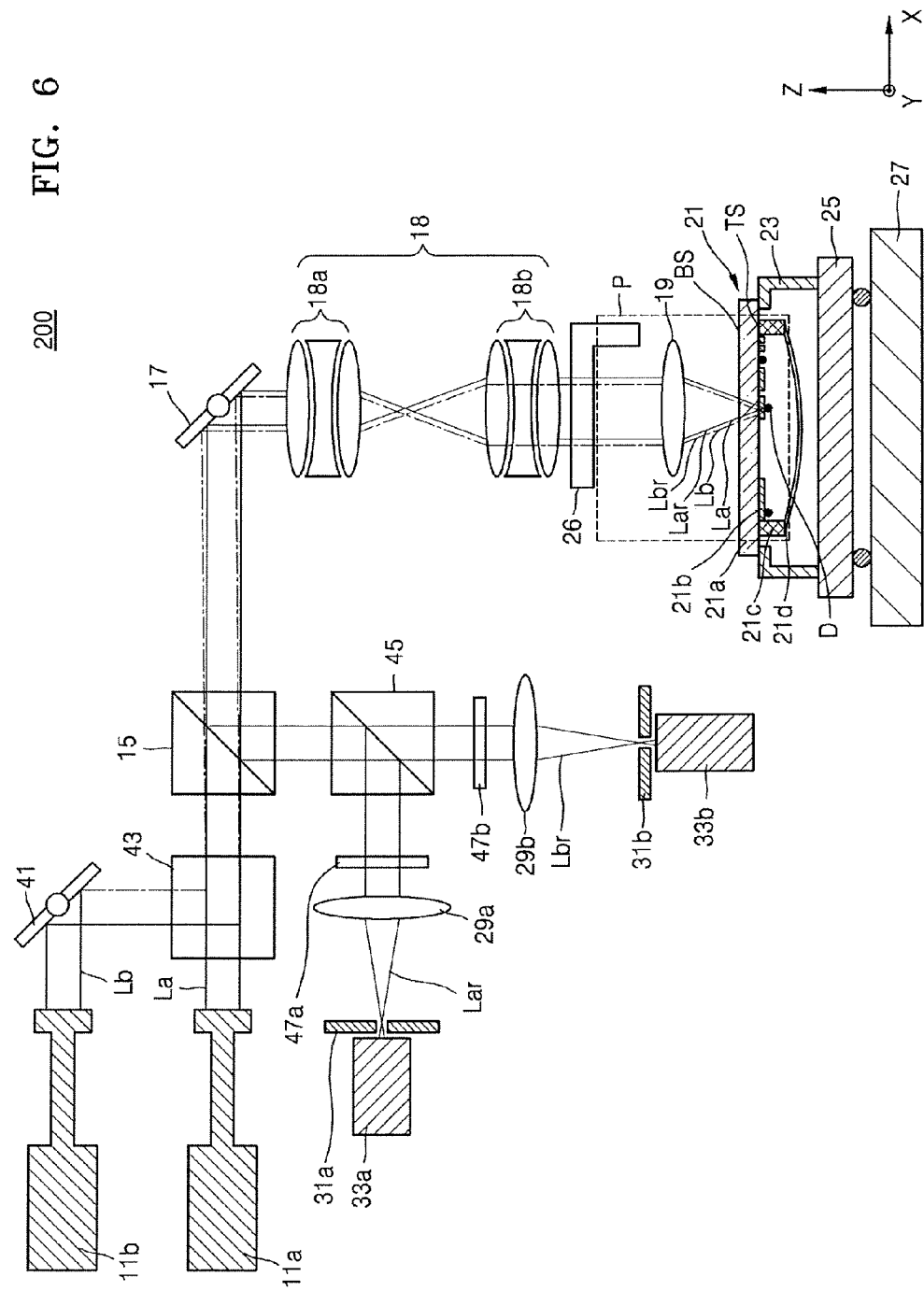
FIG. 6 is a diagram illustrating an optical inspecting apparatus according to an exemplary embodiment of the present inventive concept.

FIG. 6 is a diagram illustrating an optical inspecting apparatus 200 according to an exemplary embodiment of the present inventive concept.

Referring to FIG. 6, the optical inspecting apparatus 200 may include first and second light sources 11a and 11b that emit light beams La and Lb having different polarization directions from each other. The optical inspecting apparatus 200 may use a confocal optical system as in the optical inspecting apparatus 100 of FIG. 1 and form two focuses at different locations of an inspection target by using the first and second light sources 11a and 11b, and thus, inspection speed may be increased.

For example, the optical inspecting apparatus 200 may include the first and second light sources 11a and 11b, polarizing beam splitters 43 and 45, a first resonant mirror 41, a beam splitter 15, a second resonant mirror 17, a relay optical system 18, an objective lens 19, supports 23, a horizontal stage 25, a vertical stage 26, polarization plates 47a and 47b, condensing lenses 29a and 29b, light detectors 33a and 33b, and pinhole plates 31a and 31b. The first and second light sources 11a and 11b may respectively emit first and second light beams La and Lb having different polarization directions from each other. The polarizing beam splitters 43 and 45 may reflect the first and second light beams La and Lb according to the polarization directions thereof or split parallel rays from the first and second light beams La and Lb. The first resonant mirror 41 may change a path of the second light beam Lb such that the second light beam Lb is incident on the polarizing beam splitter 43. The beam splitter 15 may reflect the first and second light beams La and Lb regardless of the polarization directions or splits the parallel rays from the first and second light beams La and Lb. The second resonant mirror 17 may change respective paths of the first and second light beams La and Lb. The relay optical system 18 may adjust respective sizes of the first and second light beams La and Lb. The objective lens 19 may form a focus on a photomask 21 that is an inspection target. The supports 23 may support edges of the photomask 21. The supports 23 may be disposed on the horizontal stage 25. The vertical stage 26 may move the objective lens 19 in a vertical direction (e.g., a Z-axis direction). The polarization plates 47a and 47b may adjust respective polarization directions of reflection light beams Lar and Lbr that are reflected from the photomask 21. The condensing lenses 29a and 29b may focus the reflection light beams Lar and Lbr. The light detectors 33a and 33b may detect the reflection light beams Lar and Lbr. The pinhole plates 31a and 31b may remove noise in front of the light detectors 33a and 33b.

The first light source 11a may emit the first light beam La having a first polarization direction, and the second light source 11b may emit the second light beam Lb having a second polarization direction that is different from the first polarization direction. In an exemplary embodiment of the present inventive concept, the first light beam La and the second light beam Lb may respectively be S-waves and P-waves, or vice versa.

The second light beam Lb may be incident on the polarizing beam splitter 43 via the first resonant mirror 41. In this case, an angle of the first resonant mirror 41 may be determined such that the second light beam Lb is reflected by the polarizing beam splitter 43 and incident on the beam splitter 15 with a path which is not the same as a path of the first light beam La. Accordingly, the first light beam La and the second light beam Lb may be focused on different locations of the photomask 21.

The first light beam La transmitted through the polarizing beam splitter 43 and the second light beam Lb reflected by the polarizing beam splitter 43 may be incident on the beam splitter 15. The beam splitter 15 may transmit the parallel rays of the first and second light beams La and Lb so that the parallel rays are incident on the second resonant mirror 17.

The first and second light beams La and Lb reflected by the second resonant mirror 17 may proceed through the relay optical system 18 and the objective lens 19 and form two focuses on the top surface TS of the photomask 21.

Figure 7:
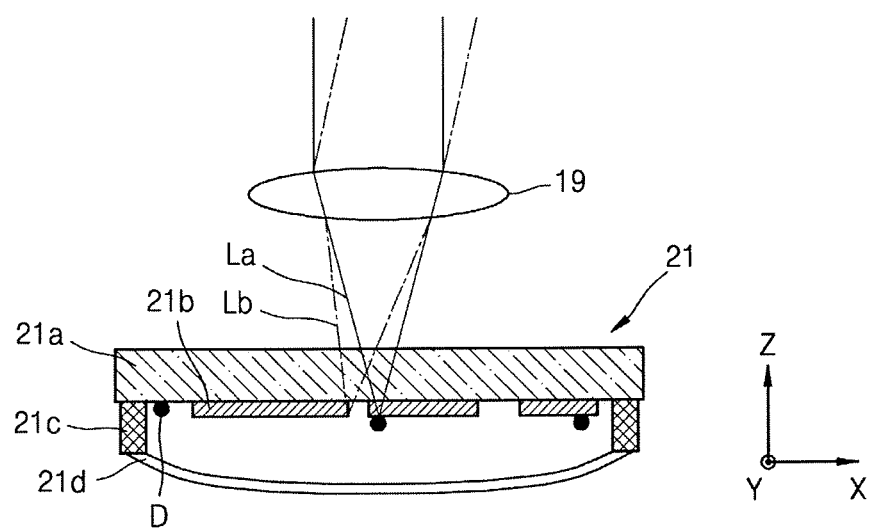
FIG. 7 is a diagram of a cross-section of a photomask on which a plurality of focuses is formed when the photomask is inspected by the optical inspecting apparatus of FIG. 6 according to an exemplary embodiment of the present inventive concept.

FIG. 7 is a diagram of a cross-section of a photomask 21 on which a plurality of focuses is formed when the photomask 21 is inspected by the optical inspecting apparatus 200 of FIG. 6 according to an exemplary embodiment of the present inventive concept.

FIG. 7 illustrates in detail the first and second light beams La and Lb at a point P near the photomask 21 of FIG. 6. As described above, the first light beam La and the second light beam Lb may commonly pass through the polarizing beam splitter 43, the beam splitter 15, the resonant mirror 17, the relay optical system 18, and the objective lens 19 of FIG. 6. Respective paths of the first and second light beams La and Lb are differently adjusted by using the first resonant mirror 41 disposed in front of the second light source 11b so that two different focuses are formed on the top surface TS of the photomask 21 to be captured. The first and second light beams La and Lb may be incident on a bottom surface BS of the photomask 21 in different paths from each other, may transmit through the transparent substrate 21a, and may form two different focuses on the top surface TS of the photomask 21. The first light beam La forms a first focus at the defect D on the photomask pattern 21b, and the second light beam Lb forms a second focus at a location different from the first focus. Accordingly, the optical inspecting apparatus 200 may simultaneously capture images corresponding to two points by using the first and second light sources 11a and 11b. Therefore, the optical inspecting apparatus 200 may be a confocal optical system whose inspection speed is increased, for example, when 2D image is obtained.

Referring back to FIG. 6, the reflection light beams Lar and Lbr reflected from the top surface TS of the photomask 21 may be transmitted to the objective lens 19, the relay optical system 18, the resonant mirror 17, and the beam splitter 15, and incident on the polarizing beam splitter 45. The polarizing beam splitter 45 may split the reflection light beam Lar having the first polarization direction and the reflection light beam Lbr having the second polarization direction from the two reflection light beams Lar and Lbr.

The reflection light beam Lar may be transmitted to the polarization plate 47a, the condensing lens 29a, and the pinhole plate 31a, and may show a first image corresponding to the first focus using the light detector 33a. The reflection light beam Lbr may be transmitted to the polarization plate 47b, the condensing lens 29b, and the pinhole plate 31b, and may show a second image corresponding to the second focus using the light detector 33b. Since the optical inspecting apparatus 200 may simultaneously detect first and second images of two points corresponding to the first and second focuses, respectively, while using the confocal optical system, the optical inspecting apparatus 200 may perform inspection at a relatively fast speed.

In an exemplary embodiment of the present inventive concept, the inspection target (e.g., the photomask 21) may include a first surface and a second surface opposite to the first surface. In this case, the first and second light beams La and Lb may be incident on the second surface and form a plurality of focuses on the first surface, and the light detectors 33a and 33b may detect the reflection light beams Lar and Lbr reflected from the first surface, and thus, an image of the first surface may be detected.

Figure 8:
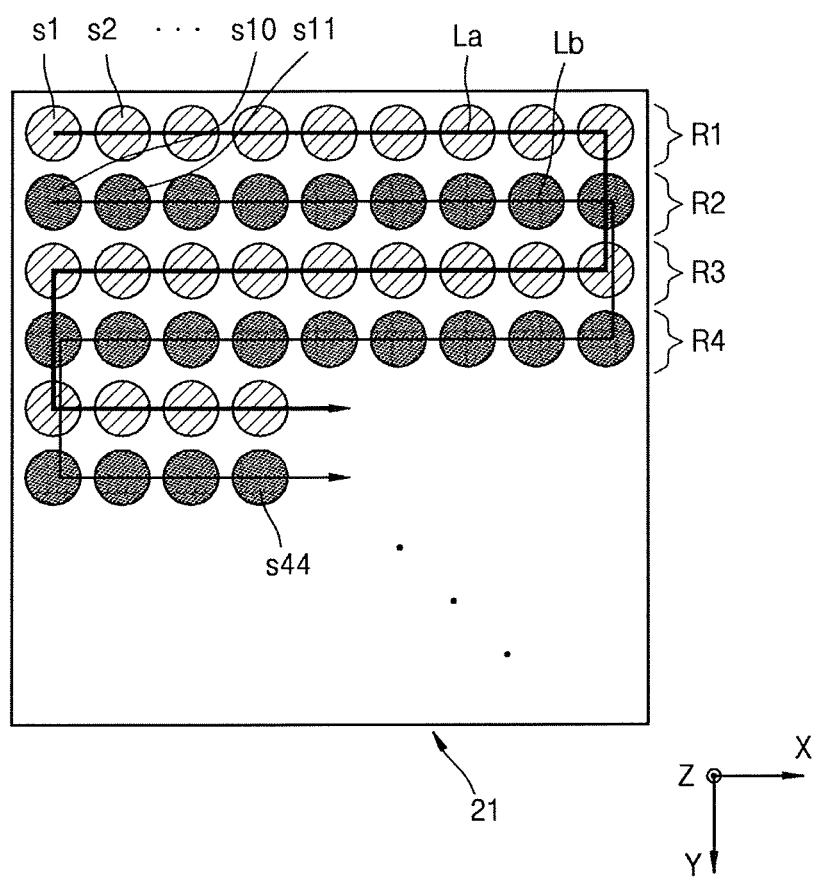
FIG. 8 is a diagram illustrating a scanning path on a photomask when the photomask is inspected by the optical inspecting apparatus of FIG. 6 according to an exemplary embodiment of the present inventive concept.

FIG. 8 is a diagram illustrating a scanning path on a photomask 21 when the photomask 21 is inspected by the optical inspecting apparatus 200 of FIG. 6. As described above, to obtain a 2D image of the photomask 21 that is the inspection target, the optical inspecting apparatus 200 may perform 2D scanning on the whole area of the photomask 21.

Referring to FIGS. 6 and 8, the whole area of the photomask 21 may be scanned by adjusting a rotation angle of the resonant mirror 17 at which the first and second light beams La and Lb are incident. In this case, a raster scanning scheme may be used, as described above. Since two focuses are formed on the photomask 21 by the first and second light beams La and Lb, two rows on the photomask 21 may be inspected at the same time.

For example, when a first row R1 including first and second spots s1 and s2 is scanned by the first light beam La, a second row R2 including tenth and eleventh spots s10 and s11 may be scanned by the second light beam Lb. When the scanning of the first row R1 performed by the first light beam La and the scanning of the second row R2 performed by the second light beam Lb are finished, respective focuses of the first and second light beams La and Lb may move on to the next two rows. In this case, since the first and second rows R1 and R2 have been simultaneously scanned by the first and second light beams La and Lb, respectively, the first light beam La that scanned the first row R1 may move on to a third row R3, and the second light beam Lb that scanned the second row R2 may move on to a fourth row R4. The resonant mirror 17 may be adjusted such that the respective focuses of the first and second light beams La and Lb move in a horizontal direction and in a vertical direction to move on to the next row when the scanning in the horizontal direction is finished. A first rotation speed when scanning in the horizontal direction may be faster than a second rotation speed when scanning in the vertical direction. A horizontal scanning speed and a vertical scanning speed may be determined respectively based on the first rotation speed and the second rotation speed.

Figure 9:
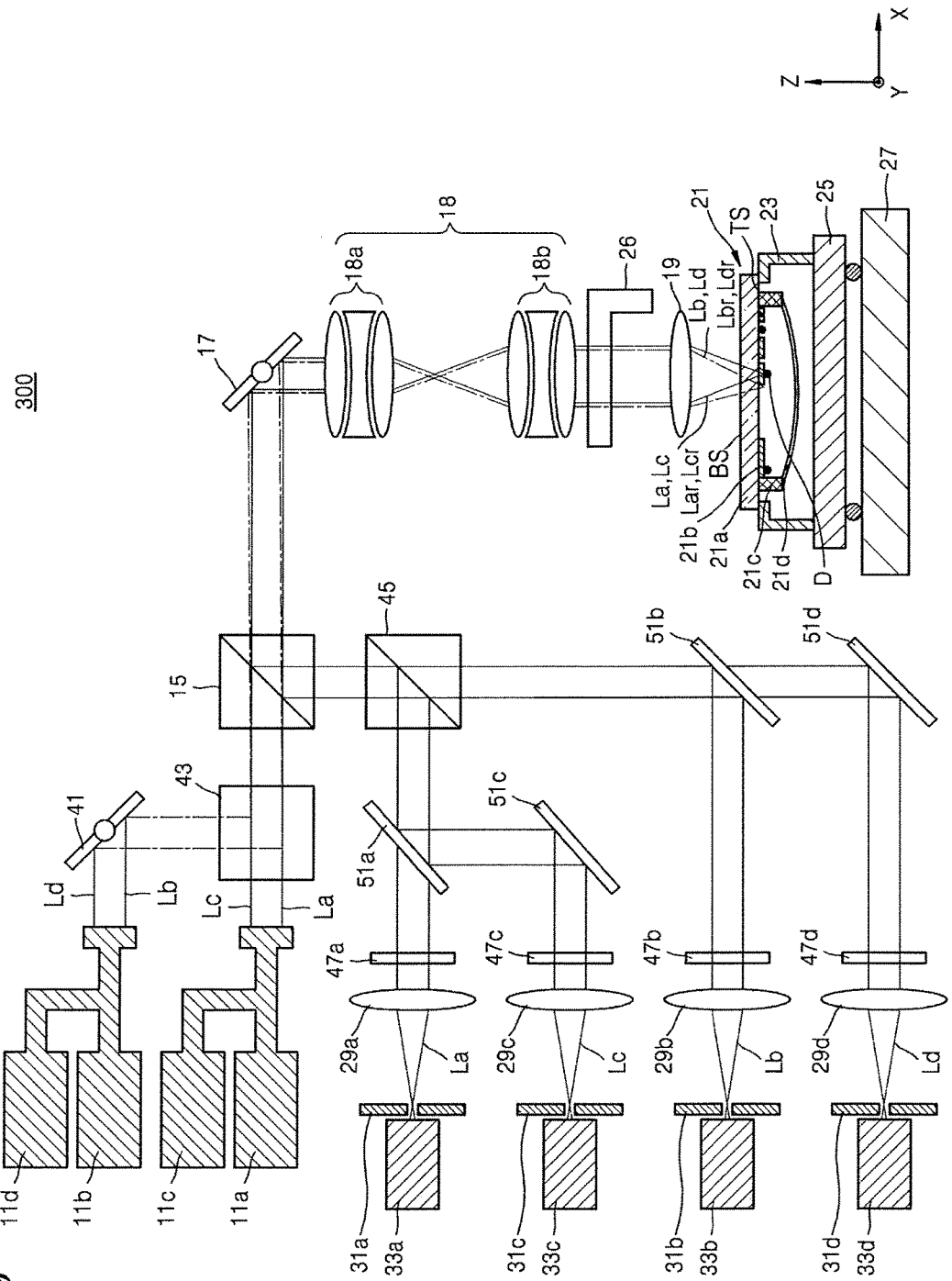
FIG. 9 is a diagram illustrating an optical inspecting apparatus according to an exemplary embodiment of the present inventive concept.

FIG. 9 is a diagram illustrating an optical inspecting apparatus 300 according to an exemplary embodiment of the present inventive concept.

Referring to FIG. 9, the optical inspecting apparatus 300 is similar to the optical inspecting apparatus 200 of FIG. 6 except that the optical inspecting apparatus 300 includes four light sources 11a, 11b, 11c, and 11d that respectively emit light beams different in at least one of a polarization direction and a wavelength from each other. The optical inspecting apparatus 300 may use a confocal optical system as in the optical inspecting apparatus 100 of FIG. 1 and form four focuses at different locations of an inspection target by using the light sources 11a to 11 d, and thus inspection speed may be increased.

For example, unlike the optical inspecting apparatus 200 of FIG. 6, the optical inspecting apparatus 300 may include a first light source 11a that emits a light beam having a first polarization direction and a first wavelength, a second light source 11c that emits a light beam having the first polarization direction and a second wavelength that is different from the first wavelength, a third light source 11b that emits a light beam having a second polarization direction and a third wavelength, and a fourth light source 11d that emits a light beam having the second polarization direction and a fourth wavelength that is different from the third wavelength.

The light sources 11a, 11b, 11c, and 11d may form four focuses on a top surface TS of a photomask 21. Four reflection light beams Lar, Lbr, Lcr, and Ldr reflected by the top surface TS of the photomask 21 may be transmitted to an objective lens 19, a relay optical system 18, a resonant mirror 17, and a beam splitter 15, and may be incident on a polarizing beam splitter 45.

The polarizing beam splitter 45 may split the reflection light beams Lar and Lcr having the first polarization direction and the reflection light beams Lbr and Ldr having the second polarization direction from the reflection light beams Lar, Lbr, Lcr, and Ldr reflected by the photomask 21. In addition, the optical inspecting apparatus 300 may further include first and second dichroic mirrors 51a and 51b. The first dichroic mirror 51a may divide the reflections light beams Lar and Lcr according to wavelengths thereof, and the second dichroic mirror 51b may divide the reflections light beams Lbr, and Ldr according to wavelengths thereof. For example, the first dichroic mirror 51a may split the first reflection light beam Lar having the first wavelength and the second reflection light beam Lcr having the second wavelength, and the second dichroic mirror 51b may split the third reflection light beam Lbr having the third wavelength and the fourth reflection light beam Ldr having the fourth wavelength. The reflection light beam Lar may be transmitted to a polarization plate 47a, a condensing lens 29a, and a pinhole plate 31a, and may show an image corresponding to a focus using a light detector 33a. The reflection light beam Lbr may be transmitted to a polarization plate 47b, a condensing lens 29b, and a pinhole plate 31b, and may show an image corresponding to a focus using a light detector 33b. The reflection light beam Lcr may be transmitted to a polarization plate 47c, a condensing lens 29c, and a pinhole plate 31c, and may show an image corresponding to a focus using a light detector 33c. The reflection light beam Ldr may be transmitted to a polarization plate 47d, a condensing lens 29d, and a pinhole plate 31d, and may show an image corresponding to a focus using a light detector 33d. Since the optical inspecting apparatus 300 may simultaneously detect images of four points corresponding to the four focuses, respectively, while using the confocal optical system, the optical inspecting apparatus 300 may perform inspection at a relatively fast speed.

Although the photomask 21 is illustrated as the inspection target of the optical inspecting apparatus 200 of FIG. 6 and the optical inspecting apparatus 300 of FIG. 9, exemplary embodiments of the present inventive concept are not limited thereto. The optical inspecting apparatuses 200 and 300 may include the confocal optical system and inspect at a relatively fast speed, and are not limited to a certain inspection target.

Although the optical inspecting apparatus 200 of FIG. 2 includes two light sources and the optical inspecting apparatus 300 of FIG. 9 includes four light sources, exemplary embodiments of the present inventive concept are not limited thereto. An optical inspecting apparatus according to an exemplary embodiment of the present inventive concept may further include a plurality of light sources that emit light beams different from each other in at least one of a polarization direction and a wavelength. For example, an optical inspecting apparatus according to an exemplary embodiment may include at least two light sources that emit light beams having different wavelengths, or an optical inspecting apparatus according to an exemplary embodiment may include a first light source that emits a light beam having a first polarization direction and a second light source that emits a light beam having a second polarization direction and a different wavelength from the first light source. Accordingly, an optical inspecting apparatus according to an exemplary embodiment of the present inventive concept may include three, five or more light sources.

While the present inventive concept has been particularly shown and described with reference to exemplary embodiments thereof, it will be understood that various changes in form and details may be made therein without departing from the spirit and scope of the present inventive concept as defined by following claims.

What is claimed is:

1. An optical inspecting apparatus comprising:
a plurality of light sources that emits a plurality of light beams;
a beam splitter that transmits or reflects the plurality of light beams;
a first lens that faces a first surface of an inspection target and forms a plurality of different focusing spots of the plurality of light beams on a second surface of the inspection target opposite to the first surface; and
a plurality of light detectors that detects a plurality of reflection light beams generated by reflecting the plurality of light beams from the second surface of the inspection target, wherein each light detector of the plurality of light detectors corresponds to a different focusing spot of the inspection target, at least two of the plurality of light beams have different polarization directions from each other or different wavelengths from each other.

2. The apparatus of claim 1, wherein the plurality of light beams is incident on the second surface, and wherein the plurality of reflection light beams corresponds to an image of the first surface.

3. An optical inspecting apparatus comprising:
a first light source that emits a first light beam having a first polarization direction;
a second light source that emits a second light beam having a second polarization direction different from the first polarization direction; a first lens that faces a first surface of a photomask, and forms a first focusing spot of the first light beam and a second focusing spot of the second light beam on a second surface of the photomask opposite to the first surface;
a first beam splitter that divides a first reflection light beam and a second reflection light beam reflected from the second surface of the photomask;
a first light detector that detects the first reflection light beam reflected from the second surface of the photomask; and
a second light detector that detects the second reflection light beam reflected from the second surface of the photomask,
wherein a photomask pattern is formed on the second surface of the photomask,
wherein each of the first and second light beams has a wavelength in an infrared range.

4. The apparatus of claim 3, further comprising pinhole plates disposed in front of the first light detector to filter noise in the first reflection light beam reflected from the second surface of the photomask.

5. The apparatus of claim 3, further comprising a second beam splitter that transmits or reflects the first and second light beams.

6. The apparatus of claim 4, wherein the first light source is a point light source, and
wherein the first light beam is converted into parallel rays and incident on the second beam splitter.

7. The apparatus of claim 3, wherein the first and second focusing spots move in a first direction to toward an edge on the second surface, and move in a second direction in which the first and second focusing spots are arranged,
wherein the first direction is substantially perpendicular to the second direction.

* * * * *